(12) United States Patent
Dunkel

(10) Patent No.: US 12,714,819 B2
(45) Date of Patent: Aug. 25, 2026

(54) CONNECTION ASSEMBLY FOR ESTABLISHING A FLUIDIC CONNECTION BETWEEN A MEDICAL DEVICE AND A PATIENT-SIDE COUPLING UNIT

(71) Applicant: Drägerwerk AG & Co. KGaA, Lübeck (DE)

(72) Inventor: Thorsten Dunkel, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 1285 days.

(21) Appl. No.: 17/609,981

(22) PCT Filed: May 8, 2020

(86) PCT No.: PCT/EP2020/062839

§ 371 (c)(1),
(2) Date: Nov. 9, 2021

(87) PCT Pub. No.: WO2020/229339

PCT Pub. Date: Nov. 19, 2020

(65) Prior Publication Data

US 2022/0203060 A1 Jun. 30, 2022

(30) Foreign Application Priority Data

May 14, 2019 (DE) .................... 10 2019 003 395.7

(51) Int. Cl.
*A61M 16/08* (2006.01)
*A61M 25/00* (2006.01)

(52) U.S. Cl.
CPC .... *A61M 16/0841* (2014.02); *A61M 16/0833* (2014.02); *A61M 16/0875* (2013.01); *A61M 2025/0004* (2013.01); *A61M 2207/00* (2013.01)

(58) Field of Classification Search
CPC .......... A61M 16/0841; A61M 16/0833; A61M 16/0875; A61M 2025/0004;
(Continued)

(56) References Cited

U.S. PATENT DOCUMENTS 4,838,258 A 6/1989 Dryden et al.
5,101,834 A 4/1992 Wallace
(Continued)

FOREIGN PATENT DOCUMENTS

CN 102274567 A 12/2011
CN 102421465 A 4/2012
(Continued)

*Primary Examiner* — Timothy A Stanis
*Assistant Examiner* — Matthew R Moon
(74) *Attorney, Agent, or Firm* — McGlew and Tuttle, P.C.

(57) ABSTRACT

A connection device for establishing a fluid connection between a medical device and a patient-side coupling unit includes a supply hose (3) connected to a patient-side connection piece (2) and connectable to the medical device. An adapter tube (13.1) of an adapter (10.1) holds a patient-side end section (EA) of a fluid measuring hose (6.1). An adapter tube holder (12.1, 12.2) of the adapter (10.1) encloses the adapter tube (13.1). The adapter tube holder (12.1, 12.2) holds the end section of the fluid measuring hose (6.1) in a predefined position relative to the patient-side connection piece (2). A measuring fluid connection can be established between the medical device and a predefined fluid sampling position (X) by the fluid measuring hose (6.1). This fluid sampling position (X) is in the interior of the patient-side connection piece (2).

20 Claims, 12 Drawing Sheets

(58) Field of Classification Search
CPC .......... A61M 2207/00; A61M 16/0816; A61M 16/085; A61B 5/097
See application file for complete search history.

(56) References Cited

U.S. PATENT DOCUMENTS

| | | | | |
|---|---|---|---|---|
| 5,284,160 | A | 2/1994 | Dryden | |
| 5,404,873 | A * | 4/1995 | Leagre | A61M 16/085 128/203.29 |
| 5,722,391 | A | 3/1998 | Rosenkoetter et al. | |
| 5,772,391 | A * | 6/1998 | Sjogren | B65H 29/003 198/470.1 |
| 10,010,690 | B1 | 7/2018 | Geraghty | |
| 12,017,000 | B2 * | 6/2024 | Landis | A61M 16/0066 |
| 2010/0286596 | A1 | 11/2010 | Hofmann et al. | |
| 2012/0013121 | A1 * | 1/2012 | Weckstrom | A61M 16/085 285/331 |
| 2012/0153613 | A1 * | 6/2012 | Kauppi | F16L 47/06 285/335 |
| 2012/0240932 | A1 | 9/2012 | Gusky et al. | |
| 2013/0102916 | A1 | 4/2013 | Colbaugh et al. | |
| 2014/0018691 | A1 | 1/2014 | Mcneill | |
| 2015/0343163 | A1 | 12/2015 | Besko | |
| 2020/0001035 | A1 * | 1/2020 | VanPelt | A61M 16/0051 |

FOREIGN PATENT DOCUMENTS

| | | | |
|---|---|---|---|
| CN | 103501848 | A | 1/2014 |
| CN | 204479255 | U | 7/2015 |
| DE | 19949283 | A1 | 4/2001 |
| DE | 69815464 | T2 | 5/2004 |
| DE | 102013018458 | A1 | 5/2015 |
| DE | 102014000101 | A1 | 7/2015 |
| EP | 2383008 | B1 | 11/2013 |
| EP | 1551486 | B1 | 4/2017 |
| WO | 2014097068 | A1 | 6/2014 |
| WO | 2017200929 | A1 | 11/2017 |
| WO | 2018104224 | A1 | 6/2018 |

* cited by examiner

P
En
2.2
2.2
2
2.1
2.1
S.a
8
S.a
9
3
L.a
L.a
S.e
L.e
1

5
20

2
8
7
3

P
En
5
20
2.2
2
2.1
8
6.3
6.1
3
9
6.2
7
4
1

P
En
2
M2
M4
M1
M3
3
Sp
1
Y
Z
X

En
2.2
2
2.1
Pl
8
L.a
9
L.a
L.e
3

10.1
13.1
12.2
12.1
En
X
2
2.2
2.1
d
EA
8
9
3
L.e
6.1

10.2
13.1
13.2
12.2
12.1
13.4
En
X
2
2.2
2.1
d
EA
8
9
6.2
3

10.3
13.1
13.3
12.2
12.1
13.4
En
X
2
2.2
2.1
d
EA
8
9
6.3
3

14.1
11.1
14.1
11.1
15.1
11.1
14.1

En
X
14.1
2
2.2
2.1
EA
12.2
12.2
12.1
12.1
8
9
L.e
6.1
3

En
X
2
14.1
EA
2.2
11.2
2.1
14.2
12.2
12.2
12.1
12.1
L.a
6.2
3
11.2
14.1
14.2

13.3
14.1
11.3
15.1
2
En
X
EA
2.2
2.1
12.2
12.1
8
9
6.3
3

CONNECTION ASSEMBLY FOR ESTABLISHING A FLUIDIC CONNECTION BETWEEN A MEDICAL DEVICE AND A PATIENT-SIDE COUPLING UNIT

CROSS REFERENCE TO RELATED APPLICATIONS

This application is a United States National Phase Application of International Application PCT/EP2020/062839, filed May 8, 2020, and claims the benefit of priority under 35 U.S.C. § 119 of German Application 10 2019 003 395.7, filed May 14, 2019, the entire contents of which are incorporated herein by reference.

TECHNICAL FIELD

The present invention pertains to a device, by means of which a fluid connection can be established between a medical device and a patient-side coupling unit. The medical device comprises, for example, a ventilator, which mechanically ventilates a patient or supports his natural breathing, or an anesthesia apparatus, which anesthetizes a patient. The coupling unit comprises, for example, a tracheostoma catheter or an endotracheal tube.

TECHNICAL BACKGROUND

A connection device, which is capable of connecting a medical device (conventional gas machine 215) to a patient-side connection device (patient end connector 14), is described in U.S. Pat. No. 5,284,160. A fluid-measuring hose (sampling hose 23, 201) is passed centrally through a coaxial hose with an outer hose (flexible outer breathing hose 27) and with an inner hose (flexible inner breathing hose 29). An adapter (sampling adapter 12) is connected to the patient-side connection piece 14 and it comprises a bracket (apertured support 22) with hubs 43 and with a central recess, through which the fluid measuring hose 23, 201 is passed.

U.S. Pat. No. 5,722,391 describes a coaxial hose for an anesthesia apparatus (anesthesia tube assembly) with an outer hose (outer tube 12) and with an inner hose (inner tube 14). The patient-side port 20 of the device comprises an outer cylinder 21, which is connected to the outer hose 12 in a gas-tight manner, as well as an inner cylinder 25, which is connected to the inner hose 14. A line (extension pipe 40) is capable of removing gas at a gas sampling point (gas sampling point 42). A gas measuring hose (gas sampling tube 38) passes through the interior of the inner hose 14 and is fastened with a clip (clip), not shown, to the inner cylinder 14 in the vicinity of the inner cylinder 25.

DE 69815464 T2 describes a mask 1 for breathing support, which comprises a tubular device 5 on the side located opposite the face 3 of the patient. This device 5 has an inner passage 7 with a conical wall 8. Ducts 9 are formed around the conical part 8 between this wall 8 and a ring-shaped chamber 12.

The device described in EP 2383008 B1 holds a volume of breathing gas, with which a living being (subject 8) is ventilated, at a desired level. A ventilator (ventilator 2) supplies the living being 8 via a first hose (first tubing 6) and receives exhaled gas via a second hose (second tubing 7). The two hoses 6, 7 may be arranged in parallel next to one another or they may be configured as a coaxial hose. An adapter 4 is connected to the two hoses 6, 7 and it branches off a gas sample at a connection element (sample output connector 10). A gas-measuring hose (sampling tube 11) leads from the connection element 10 to an analysis device (gas analyzer 12) at the ventilator 2.

WO 2017/200929 A1 describes a process and a device for measuring the carbon dioxide content in the air exhaled by a patient 201, 301 by means of side-stream kapnography. The patient is connected to a ventilator 250, 350. An adapter 220, 320 branches off breathing air into a hose 215, 315, which leads to a measuring device 210, 310.

Devices for branching off gas to be tested from a breathing air circuit for a patient and to feed it to a measuring device are described in EP 1551486 B1 and in US 20150343163 A1 as well.

A device for the mechanical ventilation of a patient is described in US 2014/0018691 A1. An oxygen source 135 supplies via a hose 136 the patient with oxygen, and a breathing mask 125 is placed over the face of the patient. Air exhaled by the patient is fed to a gas measuring device 130 via a hose 132.

SUMMARY

A basic object of the present invention is to provide a connection device for establishing a fluid connection between a medical device and a patient-side coupling unit, wherein the connection device makes possible a more reliable monitoring of a fluid stream in the fluid connection established than do prior-art connection devices.

The connection device according to the present invention is configured to establish a fluid connection between a medical device and a patient-side coupling unit. The patient-side coupling unit can be coupled with a patient or be placed at the patient in another manner.

The connection device according to the present invention comprises a supply hose (tube),
a patient-side connection piece,
a fluid measuring hose (tube) and
an adapter.

The supply hose is connected to the medical device or can be connected to the medical device. The supply hose is connected, moreover, to the patient-side connection piece.

Viewed in the flow direction from the medical device to the patient-side coupling unit, the patient-side connection piece is located at the end of the supply hose or is positioned at a distance downstream of the supply hose. The supply hose and the patient-side connection piece establish together at least from time to time at least one fluid connection between the medical device and the patient-side coupling unit or are capable of establishing at least one such fluid connection. The patient can be supplied with fluid, especially breathing air, by means of this fluid connection.

The adapter comprises a rigid adapter tube and
an adapter tube holder.

The patient-side connection piece holds the adapter tube holder. The adapter tube holder fully or at least partially encloses the adapter tube.

The adapter tube holds a patient-side end section of the fluid measuring hose. The adapter tube holder holds hereby the end section of the fluid measuring hose, which is held by the adapter tube, in a predefined position relative to the patient-side connection piece, in one embodiment at the patient-side end of the connection piece. The adapter tube is rigid, whereas the fluid measuring hose is flexible; more precisely, it has a greater plasticity than does the adapter tube.

The connection device establishes a measuring fluid connection between a fluid measuring device and a predefined fluid sampling (tapping) position or is capable of establishing such a measuring fluid connection at least from time to time. This fluid sampling position is located in the interior of the patient-side connection piece. The measuring fluid connection provided comprises the fluid measuring hose.

In a typical application, the medical device shall supply the patient with the correct quantity of a gas, for example, with breathing air and/or an anesthetic gas. In case of a deviation between a required quantity, for example, a required flow rate, and an actual quantity, e.g., the actual flow rate, the medical device shall be actuated correspondingly in order for its mode of operation to change with the goal of providing the required quantity. In another application, the medical device shall monitor the spontaneous breathing of the patient. In order to make such a mode of operation possible, it is necessary reliably to measure the actual quantity of the gas, for example, the quantity of breathing air being fed or inhaled spontaneously or the quantity or the percentage of carbon dioxide in the air exhaled by the patient P or the percentage of an anesthetic gas in the gas being fed. The measurement must be reliable and reproducible. The fluid measuring device is capable of measuring the concentration of at least one gas and it is in a data connection with the medical device.

A fluid measuring hose is provided according to the present invention in addition to the supply hose, by means of which a fluid connection, e.g., a fluid circuit, can be established between the patient and the medical device. Thanks to this fluid measuring hose, a defined quantity of gas to be tested can be sucked and fed to the fluid measuring device permanently or also as needed from the interior of the connection device, and this fluid measuring device is in a data connection with the medical device and is located outside the connection device.

The fluid measuring hose makes it possible to remove, especially suck, the quantity to be tested at the predefined fluid sampling position. This fluid sampling position is located according to the present invention in the interior of the patient-side connection piece. Viewed in the flow direction from the medical device to the patient, the fluid sampling position is located consequently at the end of the supply hose or downstream of the supply hose and relatively close to the patient. Consequently, a relatively small enclosed volume, in which fluid, which could distort a measurement, could collect, is located between a patient-side coupling unit and the fluid sampling position. The embodiment according to the present invention, in which the fluid sampling position is present, is especially important when the supply hose contains at least two parallel lumina, especially one for the inhalation (breathing in) and another one for the exhalation (breathing out), and it makes therefor a fluid circuit possible. The fluid sampling position can be arranged between these two lumina and the patient-side coupling unit. The measurement sought can thus be carried out in a reliable manner both during an inhalation phase and during an exhalation phase of the patient.

The possibility that the connection device and hence the fluid sampling position move relative to the patient should be taken into consideration. For example, the patient is moving or is moved, or the connection device is exposed to another force acting from outside. In addition, a so-called rinsing flow or circulating flow, which likewise exerts a force on the fluid measuring hose, is frequently flowing permanently through a connection device. The fluid sampling position should not preferably possibly perform any movement relative to the patient-side connection piece nor any movement relative to the patient-side coupling unit in this situation, either, because such a relative movement could distort the measurement results.

The end section of the fluid measuring hose is held according to the present invention by the adapter tube, doing so in a predefined position relative to the patient-side connection piece. It is ensured hereby that the fluid sampling position does not essentially perform any undesired relative movement relative to the patient-side connection piece.

The patient-side end section is held according to the present invention by means of a tube, i.e., flatly along a section of the fluid measuring hose. The patient-side end of the rigid adapter tube is located according to the present invention at the fluid sampling position. These features reduce the risk of an undesired relative movement compared to a possible embodiment in which the flexible fluid measuring hose is located loosely in the supply hose or in the patient-side connection piece or is held at one point only.

In particular, the following two alternative embodiments are possible for embodying the present invention:

1. The patient-side end of the adapter tube is located at the fluid sampling position. The patient-side end of the fluid measuring hose has a distance from this fluid sampling position. The adapter tube bridges over this distance, has a fluid-tight jacket surface and is in fluid communication with the fluid measuring hose.
2. The patient-side end of the fluid measuring hose is located at the fluid sampling position and is held there by the adapter tube. The patient-side end of the adapter tube is located at the fluid sampling position in this embodiment as well.

According to the first alternative, the rigid adapter tube makes the flexible fluid measuring hose longer towards the fluid sampling position. The adapter tube may be configured such that it can be reliably connected to the adapter tube holder and hence to the patient-side connection piece, for example, by being manufactured from the same material, which is preferably a rigid material, for example, from a rigid plastic. It is possible that the patient-side connection piece and the entire adapter form together a single component. The fluid measuring hose may, by contrast, be manufactured from a flexible material, for example, PVC or silicone. The patient-side end of the fluid measuring hose can be connected to the adapter tube in an area that has a distance from the fluid sampling position. The connection between the fluid measuring hose and the adapter tube therefore influences the fluid sampling position less than if the connection were arranged at the fluid sampling position.

According to the second alternative, the adapter tube has essentially the function of holding the fluid measuring hose and of avoiding an undesired relative movement. Thanks to the adapter tube, the patient-side end of the fluid measuring hose remains in the fluid sampling position. The adapter tube does not necessarily need in the second alternative to have a fluid-tight configuration, which simplifies the manufacture. Since the patient-side end of the adapter tube is located in the fluid sampling position in this embodiment as well, the risk of an undesired relative movement is reduced compared to another positioning of the adapter tube.

According to the present invention, the connection device is capable of establishing a measuring fluid connection between the medical device and a predefined fluid sampling position. This measuring fluid connection preferably connects the fluid sampling position to a fluid measuring device, which is in a data connection with the medical device.

In one embodiment, the patient-side connection piece encloses the adapter tube holder and hence also the adapter tube. In one embodiment, when viewed in a flow direction from the medical device to the patient-side coupling unit, the dimension of the part of the adapter tube that is located in the adapter tube holder is at least half and preferably at least two thirds the dimension of the patient-side connection piece in this flow direction. As a result, the adapter tube bridges over at least half of the patient-side connection piece.

In one embodiment, the patient-side connection piece encloses the adapter tube holder in a fluid-tight manner. In another embodiment, the adapter tube holder encloses the patient-side connection piece in a fluid-tight manner. Both embodiments lead to a further reduction of the risk of fluid entering into the measuring fluid connection from outside and of distorting the measurement results that are obtained by means of the fluid measuring hose.

According to the present invention, the adapter tube holds the patient-side end section of the fluid measuring hose. In one embodiment, the adapter tube encloses the end section being held. In another embodiment, the end section of the fluid measuring hose, which end section is being held, encloses the adapter tube in a fluid-tight manner. Both embodiments may be embodied especially in combination with the above-described first embodiment, in which the adapter tube bridges over a distance between the fluid sampling position and the patient-side end of the fluid measuring hose. The embodiment in which the adapter tube encloses the end section in a fluid-tight manner or vice versa leads to an especially reliable holding of the fluid measuring hose and reduces the risk of fluid entering from outside and distorting the measurements.

In one embodiment, an end piece of the supply hose is connected to the adapter tube holder in a fluid-tight manner. This embodiment also reduces the risk of measurements being distorted. On the one hand, gas could escape, bypass the adapter tube holder and reach the fluid sampling position without such a fluid-tight connection. On the other hand, fluid could enter into the supply hose from outside.

The adapter tube is preferably arranged fully or at least partially in the interior of the patient-side connection piece. As a result, the patient-side connection piece encloses the adapter tube at least partially and protects the adapter tube from mechanical stresses, which act from outside. The adapter tube does not therefore need to be made thicker than necessary in order to hold the fluid measuring hose and to make sampling of fluid possible in a reliable procedure.

In one embodiment, the patient-side end section of the fluid measuring hose is clamped in the interior of the adapter tube. Or else, the adapter tube is clamped in the interior of the end section. The adapter tube is, in turn, permanently connected to the adapter tube holder. This embodiment holds the patient-side end section of the fluid measuring hose especially securely and prevents the fluid measuring hose from performing an undesired movement relative to the fluid sampling position. In a preferred configuration of this embodiment for holding the patient-side end section, the patient-side end section is clamped in the interior of the adapter tube. The internal diameter of the adapter tube can be increased against a restoring force, for example, based on an elasticity and/or plasticity of the adapter tube. The restoring force clamps the patient-side end section in the interior of the adapter tube.

The predefined fluid sampling position is located according to the present invention in the interior of the patient-side connection piece or in the interior of the adapter. In one embodiment, the fluid sampling position is located in the interior of the patient-side connection piece and at a spaced location from the patient-side end of this connection piece or at this patient-side end. The patient-side connection piece is, as a rule, larger and often also more mechanically robust than the adapter, so that it is advantageous to specify the fluid sampling position with reference to the patient-side connection piece.

The fluid sampling position is preferably located on an imaginary central axis of the supply hose or on an imaginary extension of this central axis towards the patient. Different positions of how the adapter tube is arranged relative to the supply hose are possible.

The central axis of the patient-side connection piece preferably continues in the central axis of the supply hose. In one embodiment, the fluid measuring hose and the adapter tube are arranged in a centered manner relative to the supply hose and hence also relative to the patient-side connection piece.

A distance develops between the central axis of the supply hose and the central axis of the adapter tube and/or the central axis of the fluid measuring hose in an alternative embodiment. In a variant of this alternative embodiment, the adapter tube is in fluid communication with a connection tube. This connection tube is preferably in fluid communication with the fluid measuring hose. The connection tube is positioned at right angles or obliquely to the central axis of the supply hose. This variant may be combined with the first embodiment, in which the adapter tube bridges over a distance between the fluid sampling position and the patient-side end section of the fluid measuring hose. The fluid measuring hose is extended by means of the adapter tube and of the connection tube up to the fluid sampling position, which may be arranged in a centered manner, i.e., especially on a central axis of the patient-side connection piece.

The patient-side connection piece preferably holds the adapter. In one embodiment, the adapter is permanently connected to the patient-side connection piece. This configuration increases the mechanical stability and the reliability of operation of the connection device. In a variant of this configuration, the patient-side connection piece and the adapter are made in one piece, i.e., they form a single component. This leads to a further increase in the mechanical stability. The patient-side connection piece and the adapter especially preferably even have a monolithic configuration, i.e., they are manufactured in a single process step during the manufacture of the connection device, for example, by injection molding. This embodiment reduces the manufacturing costs and/or the needed manufacturing time compared to other possible embodiments.

The adapter tube is preferably connected permanently to the patient-side end section of the fluid measuring hose. The adapter tube holds in this embodiment a complete end section of the fluid measuring hose, which reduces the risk of an undesired relative movement of the fluid measuring hose compared to an only punctiform holding. The connection is established especially preferably by a bonded connection or by a welded connection.

The fluid measuring hose may be located outside the supply hose. In a preferred embodiment, the fluid measuring hose is located, by contrast, in the interior of the supply hose and is passed through the supply hose. The supply hose encloses in this embodiment the fluid measuring hose, which saves space and reduces the risk of mechanical damage to the fluid measuring hose or of being torn out of the desired position.

The supply hose may form only a single fluid connection in one embodiment. In one preferred embodiment, the supply hose is embodied, by contrast, as a multi-lumen hose, i.e., at least two fluid connections can be established simultaneously by means of the same supply hose, for example, in different directions and/or for different fluids. The at least two lumina of the supply hose are separated from one another in a fluid-tight manner. For example, the fluid stream for ventilating and anesthetizing the patient (inhalation flow) flows through one lumen and the fluid stream that occurs during the exhalation by the patient (exhalation stream) flows through the other lumen or through another lumen. The embodiment as a multi-lumen hose saves space compared to a possible embodiment with a plurality of parallel supply hoses. The fluid measuring hose is preferably passed through one of these lumina. It may be passed, in particular, through the inhalation lumen or through the exhalation lumen. It is also possible that a third lumen will form or accommodate the fluid measuring hose.

Different embodiments are possible for manufacturing the connection device according to the present invention. In one embodiment, the connection device according to the present invention is manufactured by a process that comprises the following steps:

- The fluid measuring hose is pushed into the supply hose from one side. The fluid measuring hose is pushed to the extent that a patient-side end section of the fluid measuring hose will protrude over the supply hose.
- The adapter is moved from the other side towards the supply hose. The protruding patient-side end section is pushed during this movement into the adapter tube.
- The adapter is connected now to the patient-side connection piece.

In addition, the adapter is connected to the supply hose.

This embodiment makes it possible to manufacture different components of the connection device separately from one another and to assemble them only at the location of use.

The present invention will be described below on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
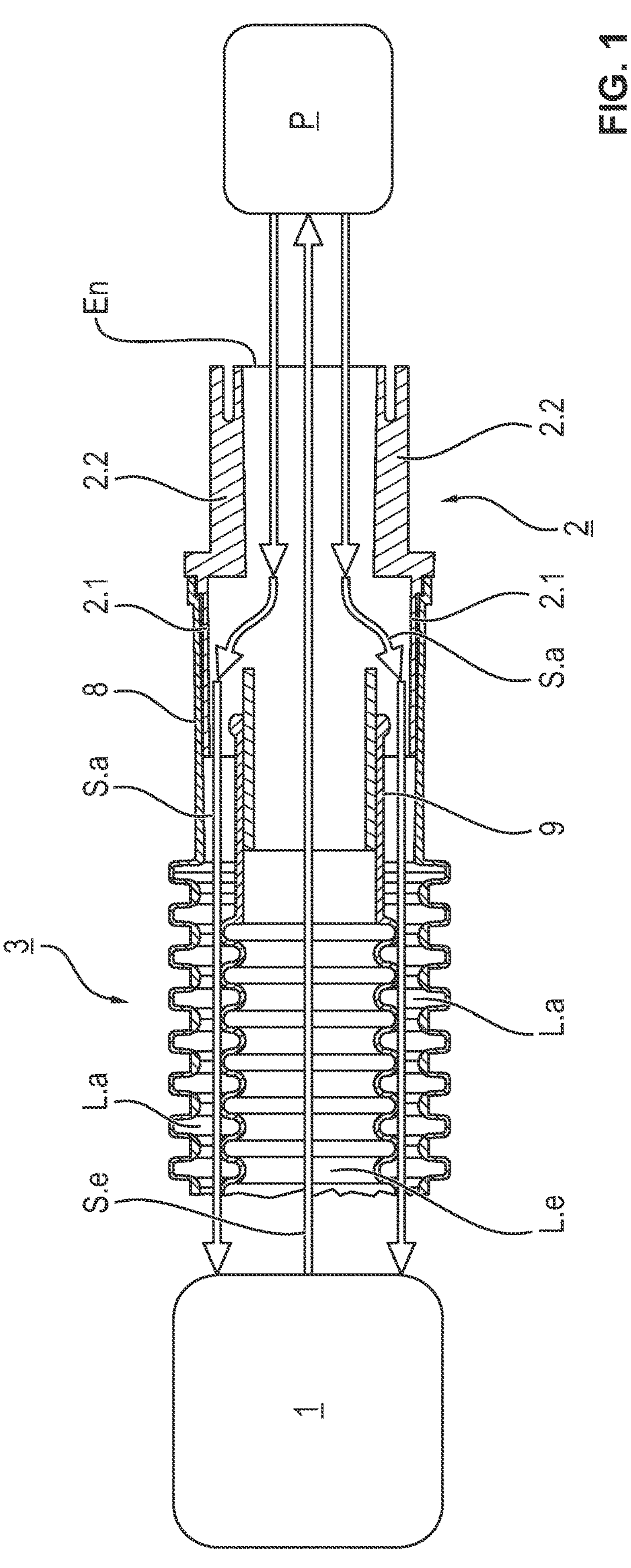
FIG. 1 is a schematic sectional view showing a connection device between a medical device and a patient.
Figure 2:
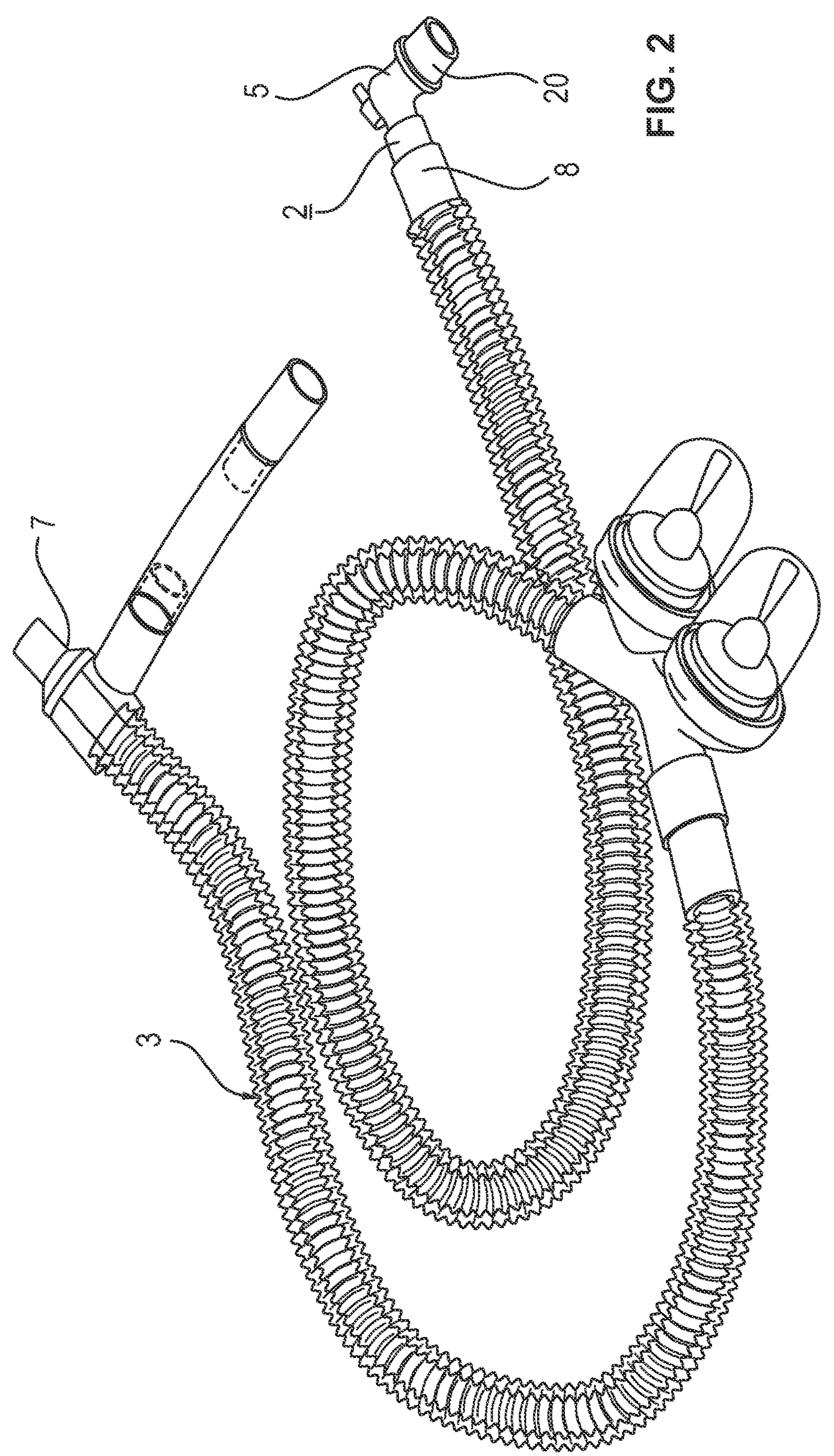
FIG. 2 is a perspective view showing the connection device.
Figure 3:
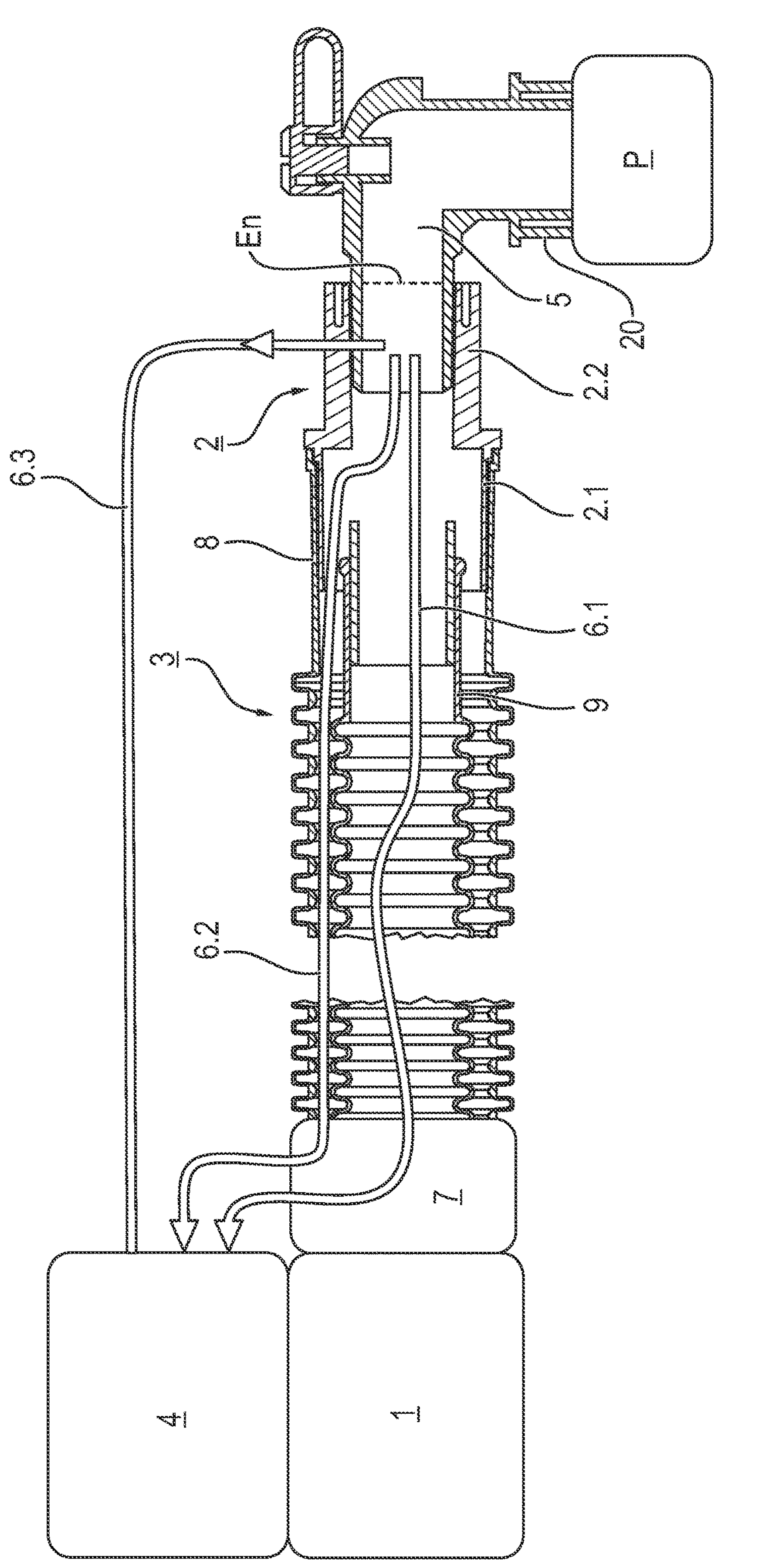
FIG. 3 is a schematic sectional view showing three possible courses of a gas measuring hose, which carries gas to a gas measuring device.
Figure 4:
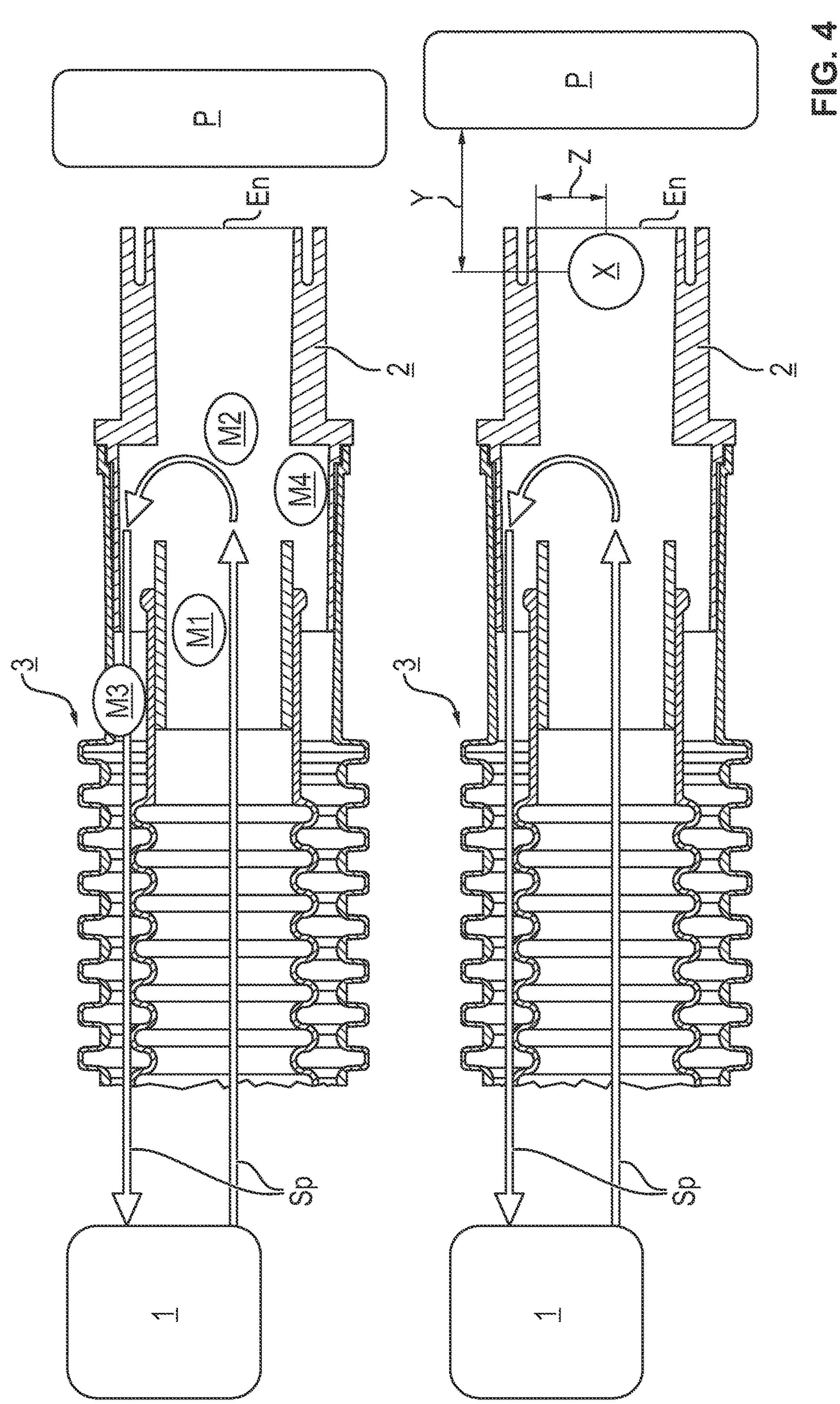
FIG. 4 is a schematic sectional view showing four disadvantageous measurement positions and one preferred measurement position at which gas is introduced into the gas measuring hose shown in FIG. 3.

Referring to the drawings, FIG. 1 through FIG. 3 show an exemplary setting, in which the present invention is used. FIG. 4 illustrates an advantage that can be achieved by the present invention, and FIG. 5 through FIG. 12 show two preferred configurations of the exemplary embodiment.

The present invention is used in the exemplary embodiment in a connection device, which connects a patient to a medical device or, more precisely, which establishes a fluid circuit between the patient and the medical device. In one configuration, the medical device comprises a ventilator. The ventilator controls especially the breathing phases of the patient and/or supports and/or stimulates his breathing. In another configuration, the medical device comprises an anesthesia apparatus, with which a patient can be anesthetized.

The connection device comprises

- a patient-side port, which is connected or can be connected to a patient-side coupling unit, which is not shown in FIG. 1, wherein the patient-side coupling unit comprises an L-shaped connection piece and a mouthpiece in the exemplary embodiment,
- a device-side port, which is connected or can be connected to the medical device and comprises, e.g., a T-piece or an end piece, and
- a multi-lumen hose (tube).

In one configuration, the connection device can be used several times. In another configuration, the entire connection device as well as the patient-side coupling unit are connected in advance into a system, and this system is transported in a suitable jacket to a location of use, it is removed from the jacket there, is connected to the patient-side coupling unit and to the medical device, it is used once to establish a fluid connection and is then disposed of.

A multi-lumen hose is defined as a hose that has at least two lumina over the entire length of the hose, wherein each lumen is separated from the other lumen or from each other lumen in a fluid-tight manner. Different fluid streams can flow as a result through the hose simultaneously, for example, in two different directions and/or such that the streams are formed by different fluids and/or at different flow rates. In particular, a ventilation circuit can be formed for a patient with a single supply hose if this is configured as a multi-lumen hose. The multi-lumen hose is configured in the exemplary embodiment as a coaxial hose. It is also possible that a membrane divides the hose along the entire length into at least two lumina, wherein each lumen adjoins from the inside an outer wall of the hose and adjoins the membrane.

The coaxial hose according to the exemplary embodiment comprises an inner hose, which forms an inner lumen, as well as an outer hose, which forms an outer lumen.

The outer hose fully encloses coaxially the inner hose in the exemplary embodiment. The inner hose with the inner lumen is used in the exemplary embodiment for the inhalation (breathing in), and the outer hose with the outer lumen is used for the exhalation (breathing out). It is also possible to use the two lumina the other way around or to use two parallel hoses. The two hoses are separated from one another in a fluid-tight manner.

FIG. 1 schematically shows this connection device between the patient and the medical device, comprising the ventilator and/or the anesthesia apparatus. Shown are:

the patient P, the medical device 1, a flexible coaxial hose 3, the inner lumen L.e formed by the inner hose of the coaxial hose 3, the outer lumen L.a formed by the outer hose of the coaxial hose, a rigid or flexible inner end piece 9 of the inner hose, a rigid or flexible outer end piece 8 of the outer hose, which fully and coaxially encloses the inner end piece 9 and protrudes over the inner end piece 9, a Y-piece 2, which is connected or can be connected to the patient-side coupling unit, and has a patient-side end En, the air stream S.e during the inhalation, which flows through the inner lumen L.e, and the air stream S.a during the exhalation, which flows through the outer lumen L.a.

The Y-piece 2 is connected on one side both to the inner hose and to the outer hose and accommodates both the inner lumen L.e and the outer lumen L.a. On the other side, the Y-piece 2 connects both lumina L.e and L.a to a connection piece to the patient-side coupling unit. The designation Y-piece is therefore used. The pieces 8 and 9 on one side and 2 on the other side are connected to one another in a fluid-tight manner, the connection being permanent or detachable. The Y-piece 2 comprises in the exemplary embodiment a part 2.1 with a larger diameter, which is connected to the coaxial hose 3, and an axially adjoining part 2.2 with a smaller diameter, which is connected to the connection piece. For example, the tubular connection piece can be inserted into corresponding recesses of the smaller part 2.2. The Y-piece 2 belongs to the patient-side connection piece of the connection device in the exemplary embodiment.

FIG. 2 shows in a perspective view an exemplary embodiment of a connection system comprising the connection device and the patient-side coupling unit. Shown are:

the coaxial hose 3 with the outer end piece 8, the Y-piece 2 and an L-shaped connection piece 5, which belongs to the patient-side coupling unit and is inserted into the part 2.2 or is enclosed by part 2.2.

The connection piece 5 is connected to the Y-piece in a fluid-tight manner, the connection being permanent or detachable. This coaxial hose 3 is flexible and can be brought into nearly any desired shape. Furthermore, a mouthpiece 20, which belongs to the patient-side coupling unit, and a T-piece 7, which belongs to the device-side port, are shown.

While the patient P is being ventilated and/or anesthetized, a gas, which is in connection with the ventilation and/or anesthesia of the patient P, shall be tested. For example, the percentage of carbon dioxide or the concentration of an anesthetic in the air fed to the patient P and/or in the air exhaled by the patient P shall be tested. Similar external conditions shall be present during this testing over a rather long time period, especially in order to make it possible to reliably assess the current status of the patient P.

FIG. 3 shows a plurality of possibilities of how such a device 4 for testing gas being fed or removed is connected to the patient P. Gas flows through a gas measuring hose (tube) 6.1, 6.2, 6.3 to a gas measuring device 4. Three possible positions of how a gas measuring hose 6.1, 6.2, 6.3 can be installed are shown, namely, a gas measuring hose 6.1 with an inhalation course in the inner lumen L.e, a gas measuring hose 6.2 with an exhalation course in the outer lumen L.a and a gas measuring hose 6.3 with an external course, i.e., outside the coaxial hose 3.

A problem that may result in case of the use of a connection device with a gas measuring hose 6.1, 6.2, 6.3 results from a curvature, which is imposed to the gas measuring hose 6.1, 6.2, 6.3 by the manufacture and the transportation to a location of use. As a rule, a roll with a long hose is manufactured. A segment of this long, rolled-up hose is cut off and used as a gas measuring hose 6.1, 6.2, 6.3. The present invention makes it possible to maintain a gas measuring hose 6.1, 6.2, 6.3 with a course that is selected from these three possible courses despite the curvature imposed on it. The position at which gas to be tested enters into the gas measuring hose 6.1, 6.2, 6.3 relative to the Y-piece 2 remains unchanged thanks to the present invention despite the imposed curvature even if the connection device is being moved.

The T-piece 7 between the coaxial hose 3 and the medical device 1 makes it possible to pass a gas measuring hose 6.1, 6.2 with the course in the interior of the coaxial hose 3 out of the coaxial hose 3. Gas to be tested enters into the gas measuring hose 6.1, 6.2 at the patient-side end.

While the patient P is being ventilated and/or anesthetized, a flow of gas is flowing from the medical device 1 through the coaxial hose 3 to the patient-side port and back again. This gas flow is called rinsing flow or circulating flow and it prevents a backup of gas in the connection device and it preferably has a constant volume flow rate. FIG. 4 shows this rinsing flow Sp. Furthermore, FIG. 4 shows in the top part of the figure four possible measurement positions M1 through M4, which have different drawbacks, and a preferred measurement position X, which can be achieved in a reliably operating manner due to the present invention, is shown in the lower part of the figure. These five measurement positions have the following meanings:

In measurement position M1, the gas measuring hose 6.1, 6.2, 6.3 ends in the inner lumen L.e. As a result, the device 4 is only capable of testing fresh breathing gas, which is flowing in the air stream S.e from the medical device 1 to the patient P, but no exhaled breathing gas in the air stream S.a.

In measurement position M2, the gas measuring hose 6.1, 6.2, 6.3 ends in the direct transition between inhalation and exhalation. This position has the drawback that the rinsing flow may distort the measurement results.

- In measurement position M3, the gas measuring hose 6.1, 6.2, 6.3 ends in the outer lumen L.a. The device 4 is capable as a result of detecting only exhaled breathing gas in the air stream S.a but no fresh breathing gas in the air stream S.e.
- In measurement position M4 the gas measuring hose 6.1, 6.2, 6.3 ends in an edge area of the Y-piece 2. There is a risk that the gas measuring hose 6.1, 6.2, 6.3 is partially or even fully closed and a valid measurement cannot be guaranteed.
- An ideal measurement position X is located outside the rinsing flow Sp and at a constant distance y to the patient P and at a constant distance z to the outer wall of the Y-piece 2.

Two embodiments of the present invention will be described below with reference to FIG. 5 through FIG. 12. The first embodiment comprises an adapter 10.1, 10.2, 10.3 with an integrated tube, into which a gas measuring hose 6.1, 6.2, 6.3 can be inserted. The second embodiment comprises an adapter 11.1, 11.2, 11.3, which accommodates the gas measuring hose 6.1, 6.2, 6.3 in the interior and holds same. In both embodiments, the adapter 10.1, 10.2, 10.3, 11.1, 11.2, 11.3 holds a patient-side end section EA of the gas measuring hose 6.1, 6.2, 6.3 such that gas to be tested is taken up at the desired measurement position X. The patient-side end of the adapter tube is located in both embodiments at the measurement position X. A distance, which is bridged over by the adapter tube, develops in the first embodiment between the patient-side end section EA and the measurement position X. The patient-side end of the gas measuring hose 6.1, 6.2, 6.3 is additionally located at the measurement position X in the second embodiment.

Figure 5:
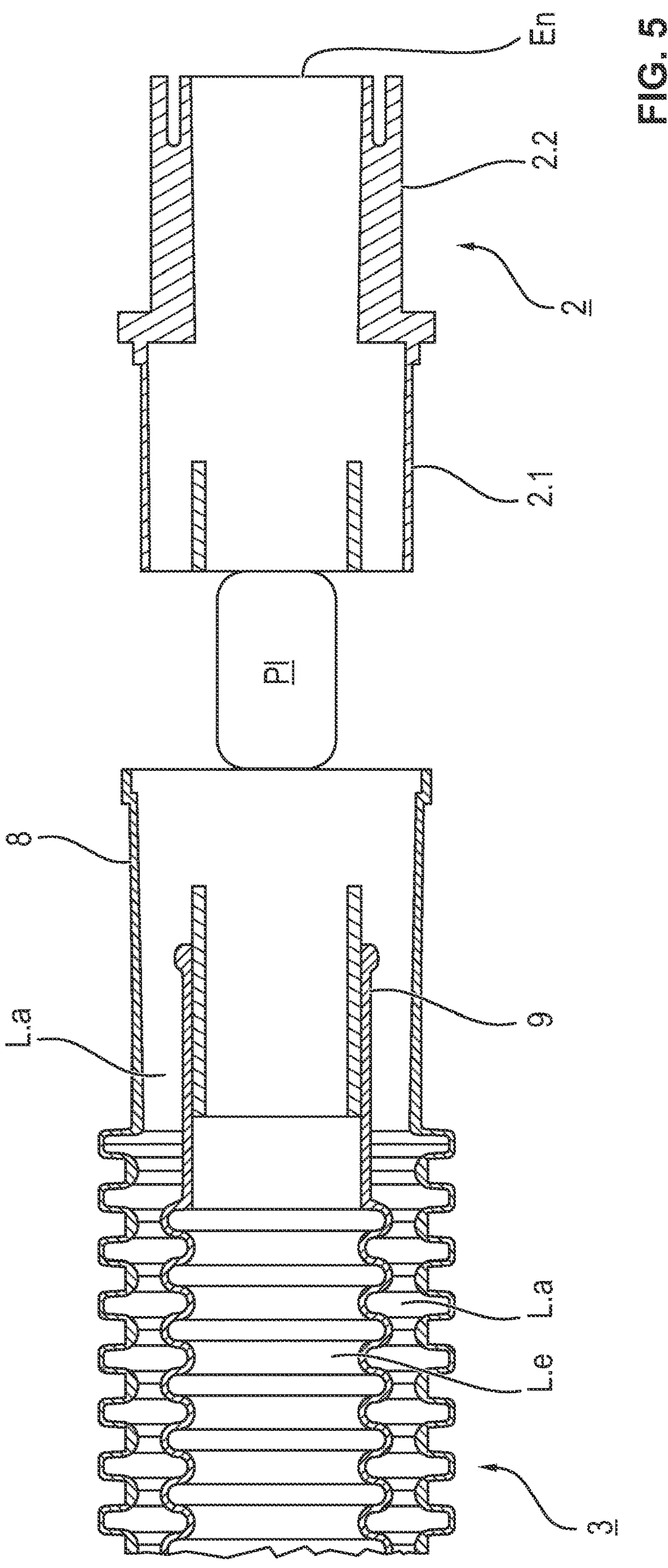
FIG. 5 is a schematic sectional view showing a possible position of an adapter between the coaxial hose and the Y-piece.

FIG. 5 shows the location Pl at which such an adapter 10.1, 10.2, 10.3, 11.1, 11.2, 11.3 for the gas measuring hose 6.1, 6.2, 6.3 can be arranged. A tube or sleeve can be inserted in both embodiments into the interior of the adapter 10.1, 10.2, 10.3, 11.1, 11.2, 11.3, so that at least one fluid connection can run through the adapter 10.1, 10.2, 10.3, 11.1, 11.2, 11.3. It is possible that this adapter 10.1, 10.2, 10.3, 11.1, 11.2, 11.3 and the Y-piece 2 are configured as a single component.

Figure 10:
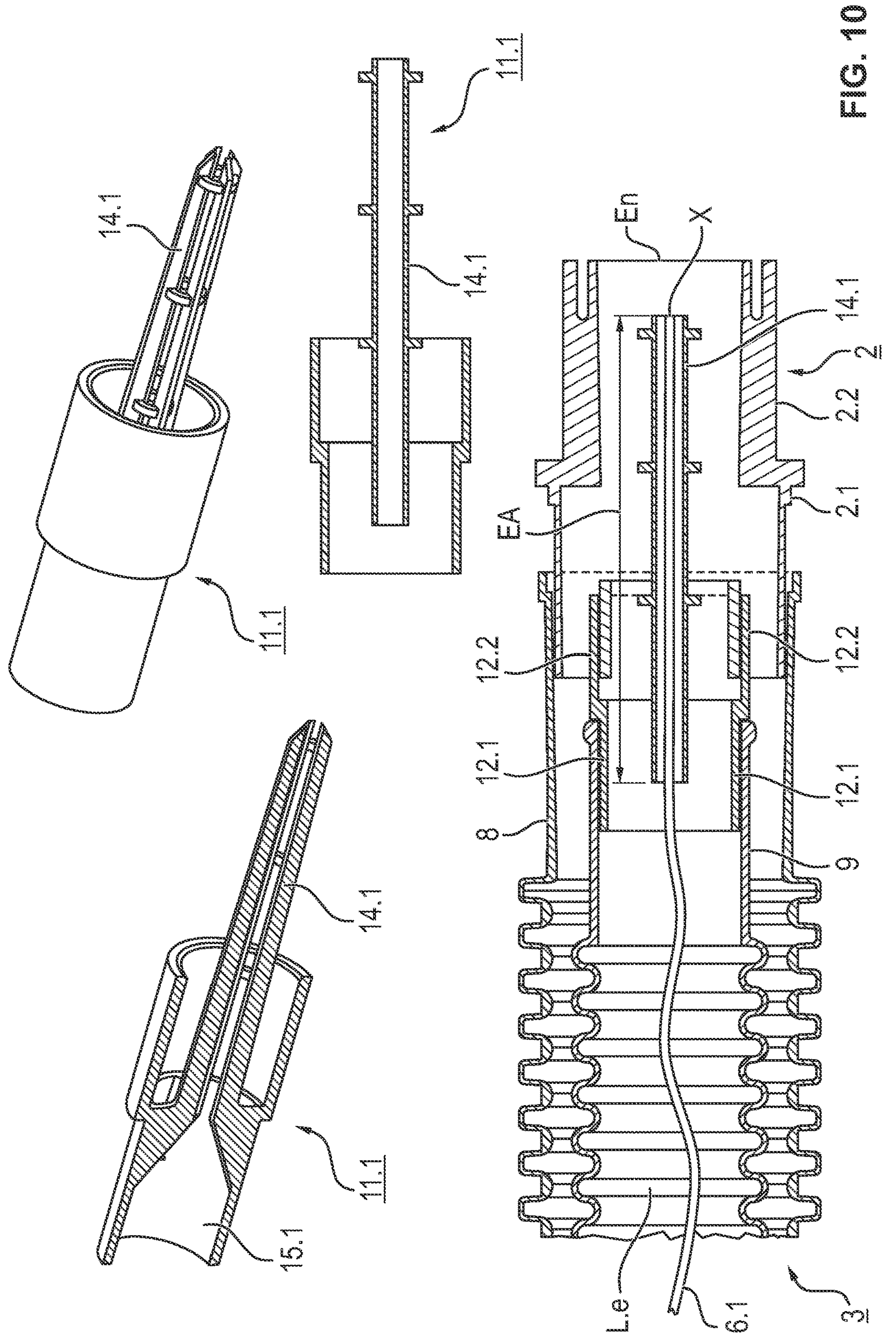
FIG. 10 shows a first configuration of a second embodiment of the adapter, which adapter holds the gas measuring hose in the inner lumen.
Figure 11:
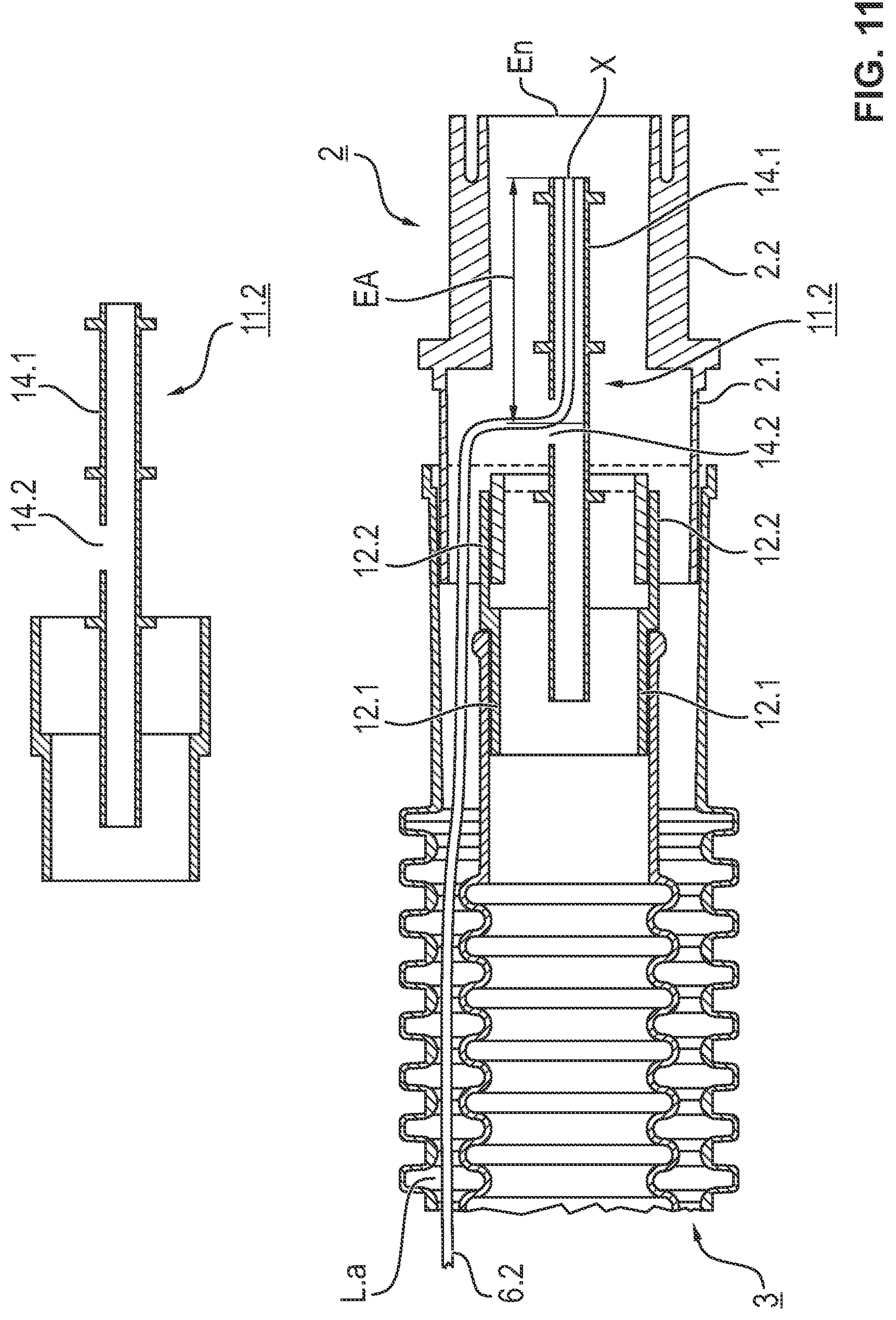
FIG. 11 shows a second configuration of the second embodiment of the adapter, which adapter holds the gas measuring hose in the outer lumen.
Figure 12:
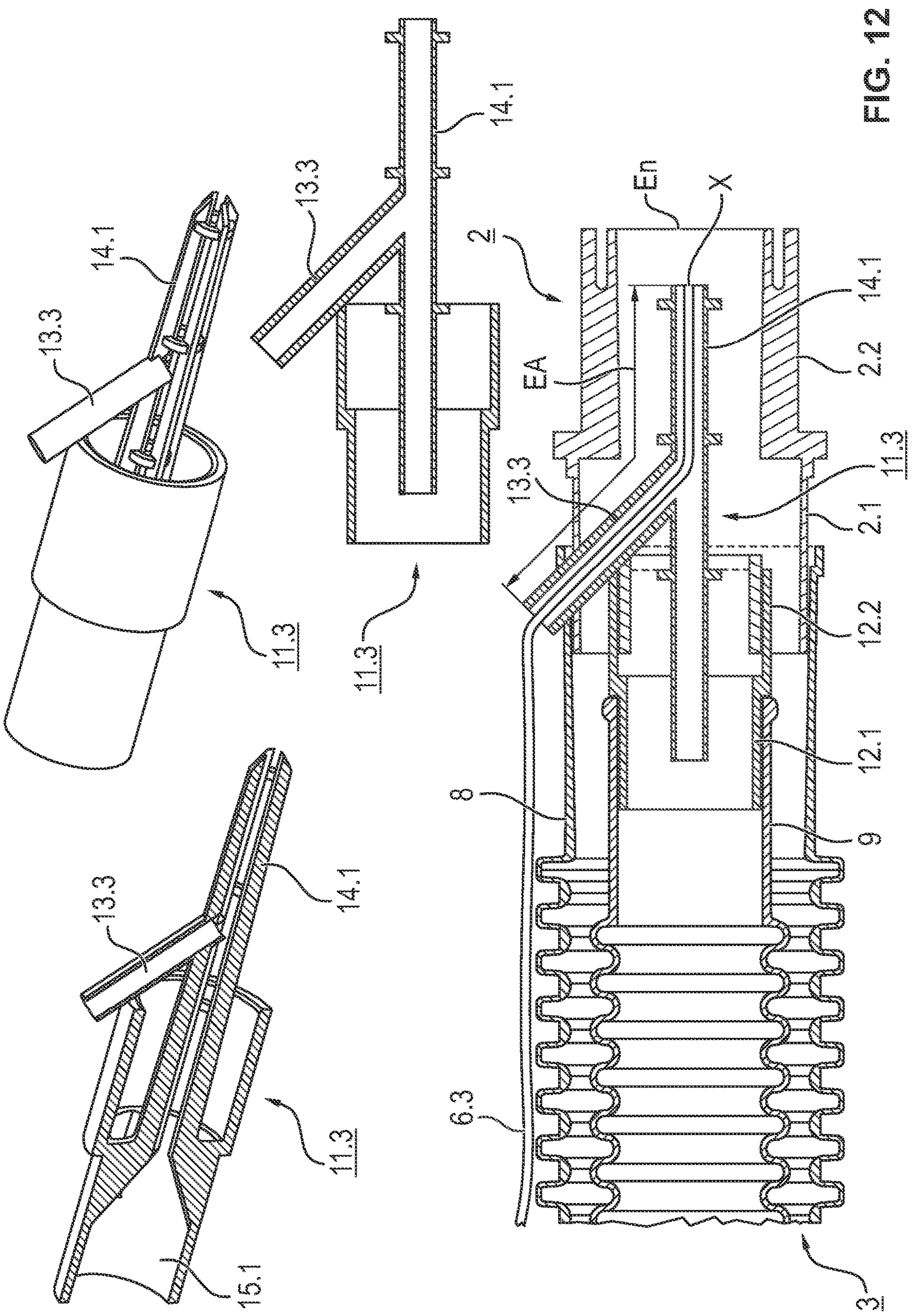
FIG. 12 shows a third configuration of the second embodiment of the adapter, which adapter holds the gas measuring hose outside the coaxial hose.

FIG. 6 through FIG. 9 show three possible configurations of the first embodiment, namely, three differently configured adapters 10.1, 10.2, 10.3. An adapter 10.1, 10.2, 10.3 according to the first embodiment may also have a combination of two or all three configurations. FIG. 10 through FIG. 12 show three possible configurations of the second embodiment. The respective ideal measurement position X achieved is shown in the figures.

Figure 6:
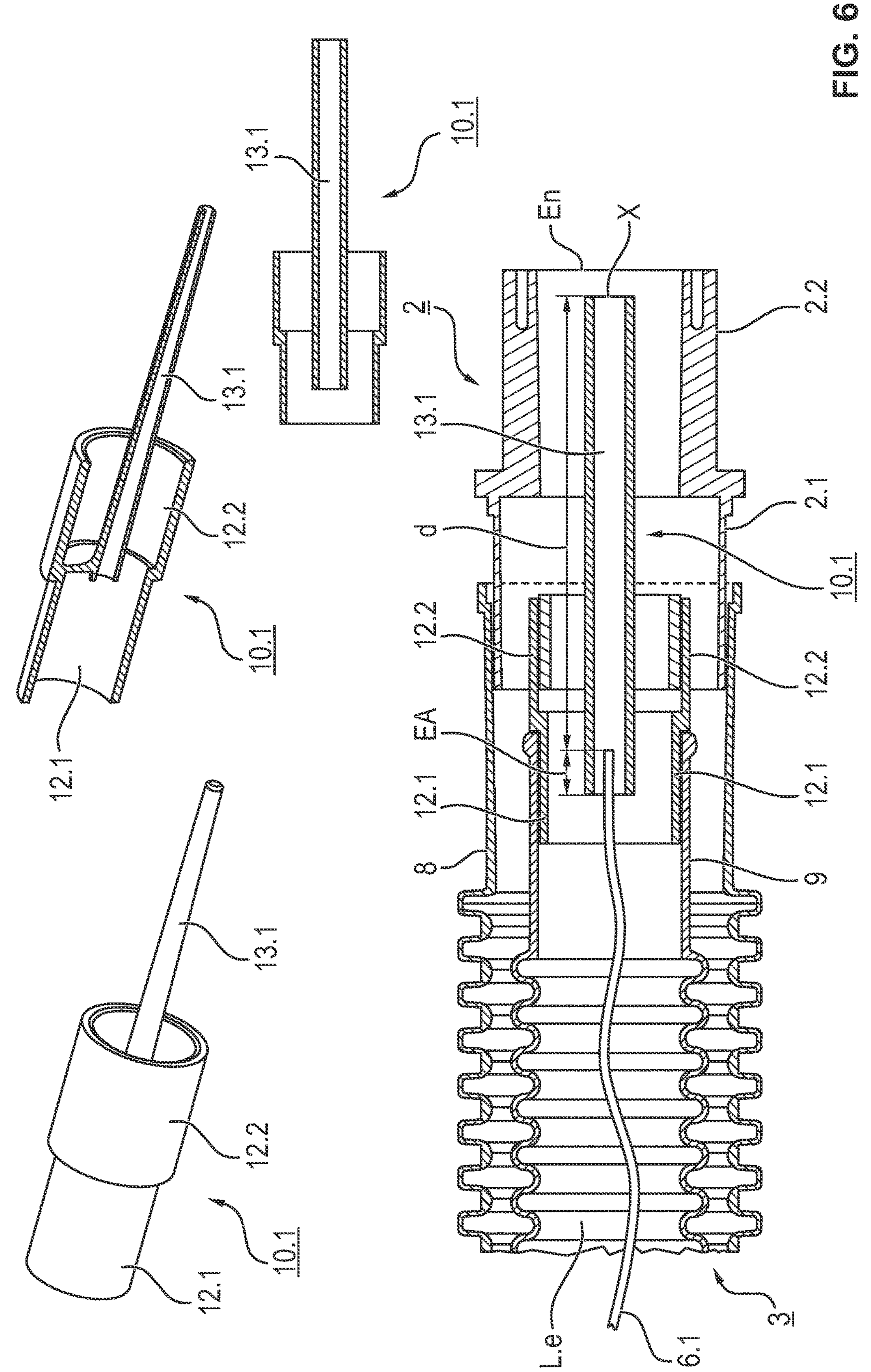
FIG. 6 shows a first configuration of a first embodiment of the adapter, which adapter holds the gas measuring hose in the inner lumen.

The adapter 10.1 according to the first configuration, which is shown in FIG. 6, is capable of holding a gas measuring hose 6.1, which is arranged in the inner lumen L.e of the coaxial hose 3, i.e., it has the inhalation course as shown and described. The adapter 10.1 comprises

- a first sleeve 12.1 with a smaller diameter,
- a second sleeve 12.2 with a larger diameter, which is permanently connected to the first sleeve 12.1, as well as
- a tube 13.1, which is passed through both sleeves 12.1, 12.2.

In the embodiment shown, the tube 13.1 protrudes over both sleeves 12.1, 12.2 towards the Y-piece 2. It is also possible that the tube 13.1 closes flush with the sleeve 12.2 or ends in the interior of the sleeve 12.1 or 12.2. The adapter 10.1 is preferably configured such that the central axes of both sleeves 12.1 and 12.2 and of the tube 13.1 are identical.

The external diameter of the smaller sleeve 12.1 is equal to the internal diameter of the inner end piece 9 in one configuration. In another configuration, the external diameter of the sleeve 12.1 is somewhat larger than the internal diameter of the end piece 9, at least at the end that adjoins the sleeve 12.2. If the sleeve 12.1 is pushed into the end piece 9, the sleeve 12.1 is compressed, or the end piece 9 is expanded.

The inner sleeve 12.1 is accommodated by the inner end piece 9 in a fluid-tight manner in all embodiments. The external diameter of the larger sleeve 12.2 is equal to the internal diameter of the segment of the Y-piece 2, which segment points towards the hose 3, or it is somewhat larger, so that the second sleeve 12.2 is received by the Y-piece 2 in a fluid-tight manner. The external diameter of the second sleeve 12.2 is preferably approximately equal to the external diameter of the inner end piece 9, so that the second sleeve 12.2 closes in a fluid-tight manner with the inner end piece 9.

In one embodiment, the adapter 10.1 is permanently connected to the Y-piece 2. It is possible that the adapter 10.1 and the Y-piece 2 are made in one piece. It is even possible that the two components 10.1 and 2 have a monolithic configuration, i.e., they are manufactured during the manufacture in a single process step and from the same material.

It is also possible that the adapter 10.1 is detachably or non-detachably connected to the Y-piece 2. An already existing Y-piece 2 can be connected with a novel type of adapter 10.1 in this alternative embodiment. It is possible, but not necessary thanks to the advantageous configuration of the present invention, to modify the Y-piece 2.

In the embodiment that is shown in FIG. 6, the tube 13.1 and hence the gas measuring hose 6.1 are in fluid communication in position with the air stream during the inhalation S.e, which flows through the inner lumen L.e. A part of the air stream S.e therefore reaches the gas measuring hose 6.1. An end piece of the gas measuring hose 6.1 is pushed into the tube 13.1. The adapter 10.1 therefore holds the gas measuring hose 6.1 in the inhalation position as shown. The adapter 10.1 is held by the Y-piece 2 and cannot move relative to the Y-piece 2. The patient-side end of the tube 13.1 is located in the measurement position X. The tube 13.1 bridges over the distance between the measurement position X and the patient-side end of the gas measuring hose 6.1 in a fluid-tight manner. The connection between the sleeves 12.1 and 12.2, on the one hand, and the tube 13.1, on the other hand, preferably has a certain elasticity, so that the distance can change reversibly and energy is absorbed. This reduces the risk of a mechanical impulse acting on the connection device damaging the gas measuring hose 6 or leading to a leak.

The tube 13.1 preferably encloses a patient-side end section of the gas measuring hose 6.1 in a fluid-tight manner. It is also possible that the gas measuring hose is connected to the tube 13.1 in a fluid-tight manner without an overlap.

In a preferred embodiment, the gas measuring hose 6.1 is permanently or detachably connected to the tube 13.1, for example, by means of a clip connection. Thanks to the present invention, it is, however, likewise possible that the gas measuring hose 6.1 is only pushed into the tube 13.1 and is held detachably, e.g., by a suitable snap holder. Thanks to the detachable connection, it is easier to clean the connection device. Both configurations reliably prevent the gas measuring hose 6 from slipping out of the tube 13.1.

In both configurations, the connection device is preferably assembled as follows:

The gas measuring hose 6.1 is pushed from the device-side port through the inner lumen L.e towards the patient-side port until it protrudes to a sufficiently great extent over the inner end piece 9.

The adapter 10.1 is pushed towards the gas measuring hose 6.1 from the other side. In one configuration, the adapter 10.1 with the Y-piece 2 is pushed towards the gas measuring hose 6.1.

A part of the protruding end of the gas measuring hose 6 is preferably connected permanently or detachably to the adapter 10.1.

The first sleeve 12.1 of the adapter 10.1 is pushed fully into the inner end piece 9 and is connected to this end piece 9 in one configuration.

The gas measuring hose 6.1 is located now in the inner lumen L.e and is held by the tube 13.1 in the inhalation course as shown.

In one configuration, the adapter 10.1 can again be pulled out of the inner end piece 9, for example, in order to clean the connection device and to attach it again.

It is not necessary in the first embodiment for an end of the gas measuring hose 6.1 to be positioned in the desired position X, which is shown in FIG. 4. It is rather sufficient to configure the adapter 10.1 such that the patient-side end of the tube 13.1 is at the measurement position X. A distance d, which is bridged over by the tube 13.1, develops between the patient-side end of the gas measuring hose 6 and the measurement position X. Gas to be tested flows from the measurement position X through the tube 13.1, which is hollow on the inside, to the patient-side end of the gas measuring hose 6 and through this to the gas measuring device 4.

In the shown embodiment of the first configuration, the tube 13.1 tapers when viewed in a direction from the coaxial hose 3 towards the Y-piece 2. It is also possible that the tube 13.1 has the same diameter over the entire length or it tapers in the other direction, i.e., towards the coaxial hose 3. It is also possible that the tube 13.1 has a convex configuration and it clamps the patient-side end of the gas measuring hose 6 in a central area of the tube 13.1.

Figure 7:
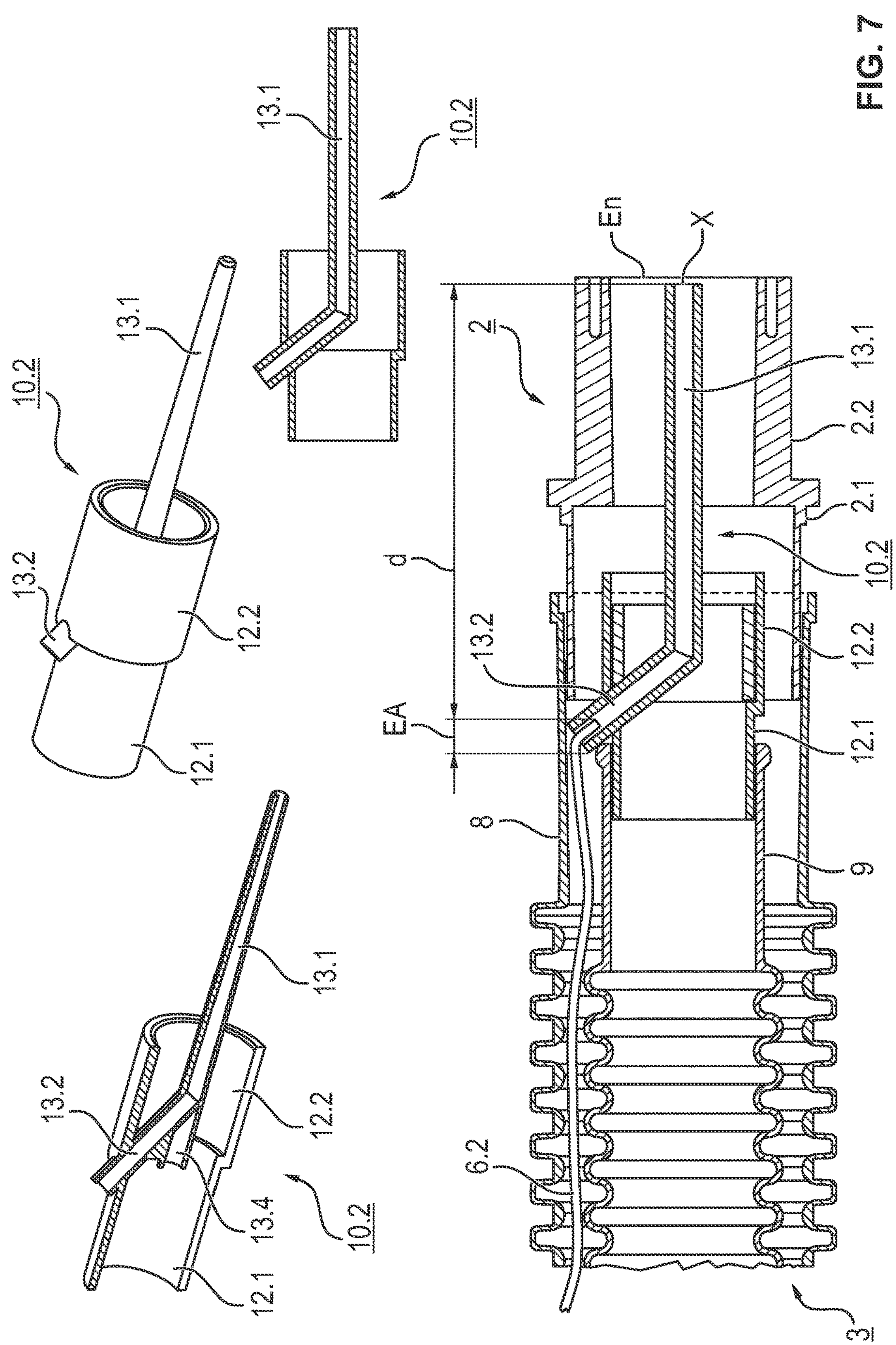
FIG. 7 shows a second configuration of the first embodiment of the adapter, which adapter holds the gas measuring hose in the outer lumen.

FIG. 7 shows a second configuration of the first embodiment, namely, the adapter 10.2. A connection tube 13.2, which is cylindrical in the configuration being shown, is pushed in the oblique or perpendicular position into the coaxially arranged tube 13.1. The connection tube 13.2 is passed through the second sleeve 12.2 and it connects the first tube 13.1 to a connection point outside the adapter 10.2. A gas measuring hose 6.2 can be inserted through the outer lumen L.a into the connection tube 13.2 and be connected to this permanently or detachably. The adapter 10.2 then holds the gas measuring hose 6 in a position that brings about an exhalation course of the gas measuring hose 6.2 as shown. The gas measuring hose 6.2 is preferably connected permanently to the device-side end of the connection tube 13.2.

Figure 8:
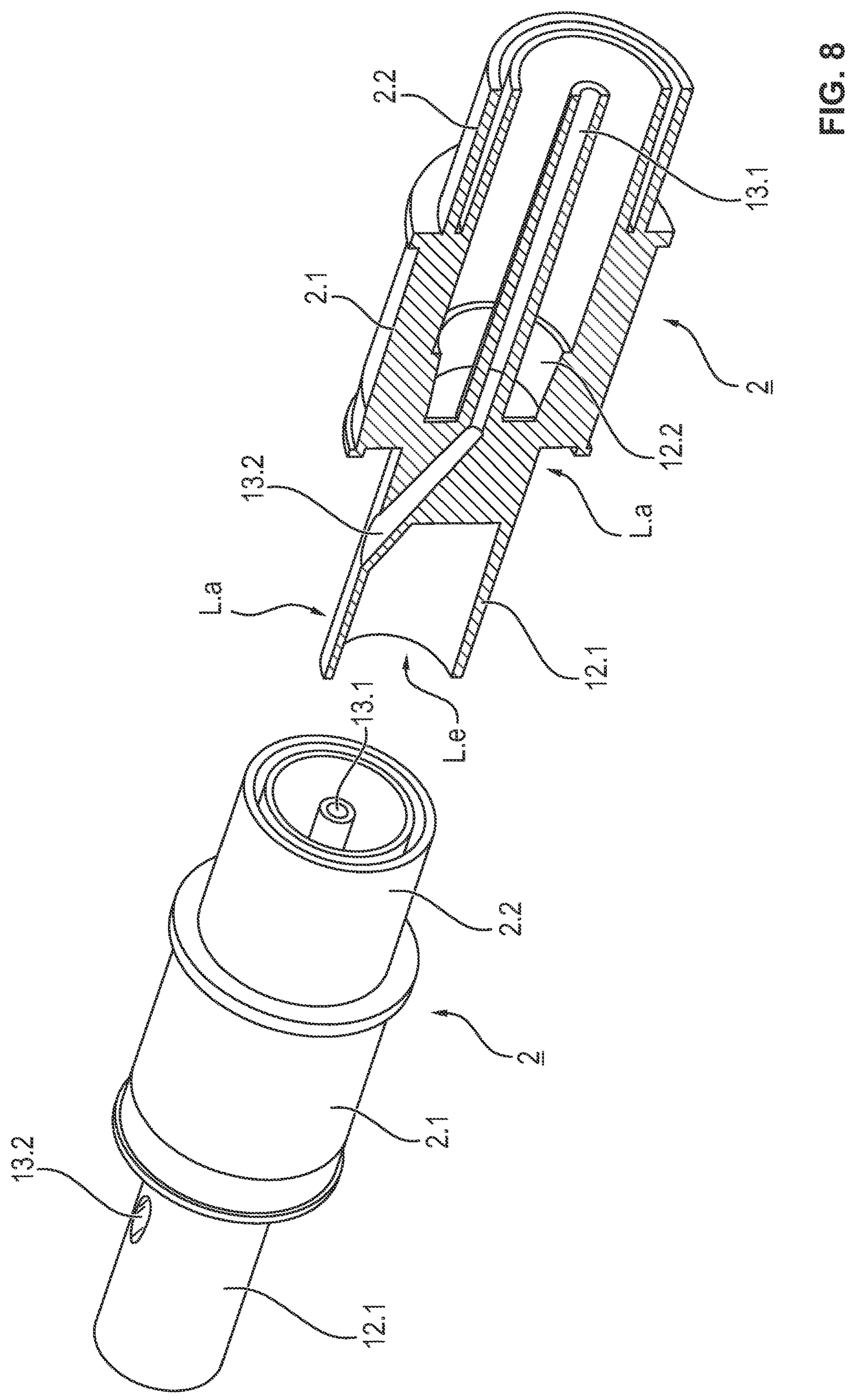
FIG. 8 is a schematic partially sectional view showing a possible configuration of the second configuration, in which the adapter and the Y-piece together form a single component.

In one embodiment, a segment 13.4 in the interior of the sleeve 12.1 and/or 12.2 protrudes over the connection tube 13.2, cf. top part of FIG. 8. It is also possible to omit this segment 13.4 and to configure the central tube 13.1 and the connection tube 13.2 together as a one-piece bent tube, cf. bottom part of FIG. 8.

The connection device with the adapter 10.2 can be assembled in exactly the same manner as the connection device with the adapter 10.1. The gas is taken again at position X, without it being necessary to move the gas measuring hose 6 itself to this position X. Gas to be tested rather flows from the measurement position X through the tube 13.1, it is deflected by the connection tube 13.2 and it then flows through the gas measuring hose 6.2 to the gas measuring device 4.

FIG. 8 shows in a perspective view (left) and in a sectional view (right) an exemplary embodiment, in which the adapter 10.2 of the second configuration and the Y-piece 2 are made in one piece. The patient-side end of the tube 13.1 closes in this example flush with the patient-side end of the smaller part 2.2 of the Y-piece 2. The tubes 13.1 and 13.2 form a one-piece bent tube.

Figure 9:
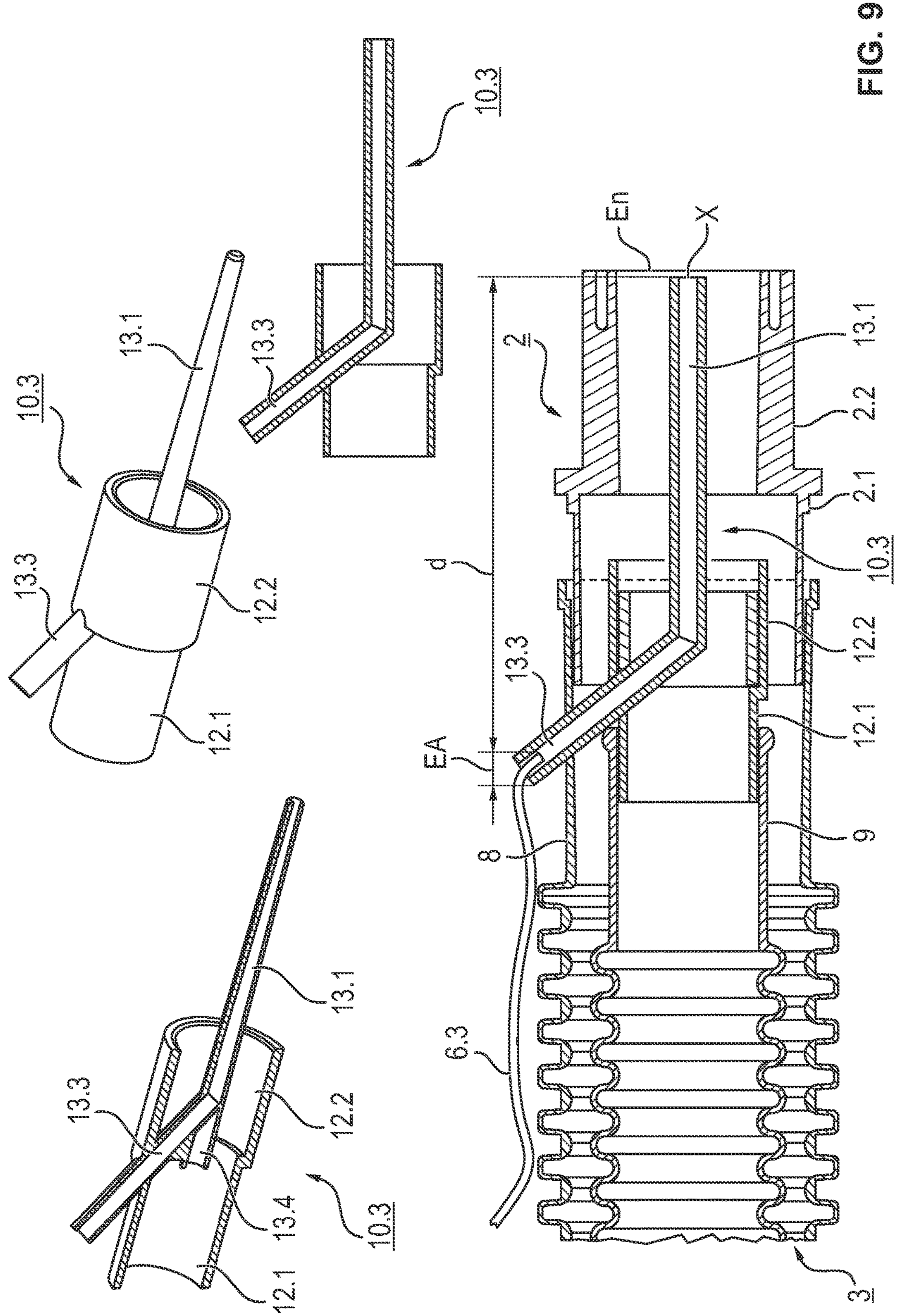
FIG. 9 shows a third configuration of the first embodiment of the adapter, which adapter holds the gas measuring hose outside the coaxial hose.

FIG. 9 shows a third configuration of the first embodiment, namely, the adapter 10.3. The connection tube 13.2 according to the second configuration is replaced with a longer connection tube 13.3. This longer connection tube 13.3 is likewise passed obliquely or at right angles through the second sleeve 12.2 and it connects the first tube 13.1 to a connection point outside the outer end piece 8. A gas measuring hose 6.3 can be inserted outside the coaxial hose 3 into the longer connection tube 13.3. The adapter 10.3 then holds the gas measuring hose 6.3 in a position that brings about an external course as shown. It is possible in the third configuration as well to omit the segment 13.4 and to configure the central tube 13.1 and the longer connection tube 13.3 as a one-piece bent tube. Gas is tapped at position X in the third configuration as well, without it being necessary to hold the gas measuring hose 6.3 itself in the desired position X.

It is common to the three configurations of the first embodiment that the gas flows from position X through an inner hollow tube 13.1 and optionally through a connection tube 13.2, 13.3 to the gas measuring hose 6.1, 6.2, 6.3. The patient-side end of the tube 13.1 is always located in the measurement position.

The adapters 11.1, 11.2, 11.3 of the second embodiment comprise instead of an inner hollow tube 13.1 a tubular guide element 14.1, wherein the gas measuring hose 6.1, 6.2, 6.3 is led through the interior of this guide tube 14.1 up to the measurement position X. Identical parts have identical reference numbers. The patient-side end of the gas measuring hose 6.1, 6.2, 6.3 and preferably also the patient-side end of the guide tube 14.1 are consequently located in the measurement position X. A patient-side segment of the gas measuring hose 6.1, 6.2, 6.3 is connected to the interior of the guide tube 14.1, for example, by bonding or welding or clipping or by a snap holder. It is possible that the guide tube 14.1 comprises two half tubes connected to one another, which clamp between them a patient-side end of the gas measuring hose 6.1, 6.2, 6.3.

The second configuration makes it possible for the gas measuring hose 6.1, 6.2, 6.3 and the guide tube 14.1 to overlap over a longer section than the gas measuring hose 6.1, 6.2, 6.3 and the tube 13.1 of the first configuration. As a result, more space is available for a permanent or detachable connection. The guide tube 14.1 compensates a curvature imposed on the gas measuring hose 6.1, 6.2, 6.3.

The adapter 11.1 brings about an inhalation course of the gas measuring hose 6.1 (FIG. 10), the adapter 11.2 has an exhalation course of the gas measuring hose 6.2 (FIG. 11) and the adapter 11.3 has an external course of the gas measuring hose 6.3 (FIG. 12). The guide tube 14.1 preferably has a plurality of ring-shaped reinforcements, which enclose the guide tube 14.1, in all three configurations. The guide tube 14.1 may have a patient-side end tapering to a tip.

The adapter 11.1 and the adapter 11.3 have a modified first sleeve with an interior space 15.1 tapering conically towards the patient-side end. The first sleeve may have exactly the same configuration as the first sleeve 12.1 of the adapter 10.1.

An opening 14.2 is prepared in the guide tube 14.1 of the adapter 11.2. The gas measuring hose 6.2 is passed through this opening 14.2 in order to bring about the exhalation course. A connection tube 13.2 may also be provided instead of the opening 14.2 just like in case of the adapter 10.2.

While specific embodiments of the invention have been shown and described in detail to illustrate the application of the principles of the invention, it will be understood that the invention may be embodied otherwise without departing from such principles.

LIST OF REFERENCE CHARACTERS

- 1 Medical device, comprises in the exemplary embodiment a ventilator, which controls the breathing phases of the patient P and/or stimulates his breathing, and/or an anesthesia apparatus, which anesthetizes the patient P, as well as the gas measuring device 4
- 2 Y-piece, connected to the end piece 9 and to the connection piece 5 in a fluid-tight manner, it accommodates the outer lumen L.a and the inner lumen L.e, is connected to the adapter 10.1, 10.2, 10.3, 11.1, 11.2, 11.3, receives the sleeve 12.2
- 3 Coaxial hose, belongs to the connection device between the patient P and the medical device 1, comprises an inner hose and an outer hose
- 4 Gas measuring device for testing a gas, for example, for determining the carbon dioxide concentration in the breathing air or the concentration of anesthetic, it is in a data connection with the medical device 1
- 5 L-shaped connection piece between the Y-piece 2 and the mouthpiece 20, belongs to the patient-side coupling unit
- 6.1 Gas measuring hose connects the testing device 4 to the Y-piece 2 with an inhalation course of the gas measuring hose in the inner lumen L.e
- 6.2 Gas measuring hose connects the testing device 4 to the Y-piece 2 with an exhalation course of the gas measuring hose in the outer lumen L.a
- 6.3 Gas measuring hose connects the testing device 4 to the Y-piece 2 with an external course of the gas measuring hose that extends outside the coaxial hose 3
- 7 T-piece between the coaxial hose 3 and the medical device 1, belongs to the device-side port of the connection device
- 8 Rigid end piece of the outer hose of the coaxial hose 3
- 9 Rigid end piece of the inner hose of the coaxial hose 3, it receives the sleeve 12.1
- 10.1 Adapter according to the first configuration of the first embodiment, it comprises a first, smaller sleeve 12.1, a second, larger sleeve 12.2 and a coaxially arranged tube 13.1 in the interior of the two sleeves 12.1, 12.2, it brings about the inhalation course 6.1
- 10.2 Adapter according to the second configuration of the first embodiment, it additionally comprises an obliquely arranged connection tube 13.2, brings about the exhalation course 6.2
- 10.3 Adapter according to the third configuration of the first embodiment, it additionally comprises an obliquely arranged, longer connection tube 13.3, brings about the external course 6.3
- 11.1 Adapter according to the first configuration of the second embodiment, it comprises the two sleeves 10.1, 10.2 and the guide tube 13.1, brings about the inhalation course 6.1
- 11.2 Adapter according to the second configuration of the second embodiment, it brings about the exhalation course 6.2
- 11.3 Adapter according to the second configuration of the second embodiment, it brings about the external course 6.3
- 12.1 First, smaller sleeve, received by the end piece 9
- 12.2 Second, larger sleeve, it adjoins the end piece 9
- 13.1 Coaxially arranged tube, it holds the gas measuring hose 6 in the inner lumen L.e (inhalation course 6.1), has a patient-side end at the measurement position X
- 13.2 Obliquely or perpendicularly arranged, shorter connection tube, it holds the gas measuring hose 6 in the outer lumen L.a (exhalation course 6.2), inserted into the tube 13.1
- 13.3 Obliquely or perpendicularly arranged, longer connection tube, it holds the gas measuring hose 6 in a position outside the coaxial hose 3 (external course 6.3), inserted into the tube 13.1
- 13.4 Segment of the tube 13.1 behind the shorter connection tube 13.2 or behind the longer connection tube 13.3
- 14.1 Tubular guide element, it holds the gas measuring hose 6
- 14.2 Opening in the tubular guide element 14.1
- 15.1 Conically tapering interior in the first sleeve 12.1
- 20 Mouthpiece, it belongs to the patient-side coupling unit, can be connected to the connection piece
- d Distance between the measurement position X and the patient-side end of the gas measuring hose 6 (first embodiment only)
- EA Patient-side end section of the gas measuring hose 6, held by the adapter 10.1, 10.2, 10.3, 11.1, 11.2, 11.3
- En Patient-side end of the Y-piece 2
- L.a The outer lumen formed by the outer hose, the air stream S.a flows through it
- L.e The inner lumen formed by the inner hose, the air stream S.e flows through it
- M1,
- . . . ,
- M4 Disadvantageous measurement positions
- P Patient
- S.a Air stream during exhalation (expiratory air stream), flows through the outer lumen L.a
- S.e Air stream during the inhalation (inspiratory air stream), flows through the inner lumen L.e
- Sp Rinsing flow in the coaxial hose 3
- X Optimal measurement position; position of the patient-side tip of the tube 13.1 (first embodiment) or of the patient-side end of the gas measuring hose 6 (second embodiment)

The invention claimed is:

1. A connection device for establishing a fluid connection between a medical device and a patient-side coupling unit, the connection device comprising:
   - a supply hose connected to or connectable to the medical device;
   - a patient-side connection piece connected to the supply hose, wherein the supply hose and the patient-side connection piece together are configured to establish a fluid connection between the medical device and the patient-side coupling unit;
   - a flexible fluid measuring hose; and an adapter comprising a rigid adapter tube and an adapter tube holder, wherein the rigid adapter tube is in fluid communication with the patient-side connection piece, wherein the patient-side connection piece holds the adapter tube holder, wherein the adapter tube holds a patient-side end section of the fluid measuring hose, wherein the adapter tube holder fully or at least partially encloses the adapter tube and holds the end section of the fluid measuring hose, which end section is held by the adapter tube in a predefined position relative to the patient-side connection piece, wherein the connection device is configured to establish a measuring fluid connection, comprising the fluid measuring hose, between a fluid measuring device and a predefined fluid sampling position, which fluid sampling position is located in an interior of the patient-side connection piece, and wherein a patient-side end of the adapter tube is located at the fluid sampling position.

2. A connection device in accordance with claim 1, wherein a distance occurs between the end section of the fluid measuring hose held by the adapter tube and the fluid sampling position, wherein the adapter tube bridges the distance, and wherein the measuring fluid connection further comprises the adapter tube.

3. A connection device in accordance with claim 1, wherein a patient-side end of the fluid measuring hose is located at the fluid sampling position in addition to the patient-side end of the adapter tube being located at the fluid sampling position.

4. A connection device in accordance with claim 1, wherein the adapter tube fluid-tightly encloses the held end section of the fluid measuring hose or the held end section of the fluid measuring hose fluid-tightly encloses the adapter tube.

5. A connection device in accordance with claim 1, wherein an end piece of the supply hose is fluid-tightly connected to the adapter tube holder.

6. A connection device in accordance with claim 1, wherein the adapter tube is arranged at least partially in the interior of the patient-side connection piece.

7. A connection device in accordance with claim 1, wherein the patient-side end section of the fluid measuring hose is clamped, based on a restoring force of the adapter tube, in an interior of the adapter tube.

8. A connection device in accordance with claim 1, wherein the fluid sampling position is located in the interior of the patient-side connection piece and at a location spaced from a patient-side end of the patient-side connection piece.

9. A connection device in accordance with claim 1, wherein the patient-side connection piece has a central axis, which is parallel to a flow direction of fluid, wherein the fluid measuring hose is positioned such that a distance occurs between the fluid measuring hose and the central axis of the patient-side connection piece, and wherein the adapter tube is in fluid communication with a connection tube, which is positioned at right angles or obliquely to the central axis of the patient-side connection piece.

10. A connection device in accordance with claim 9, wherein a distance occurs between the held end section of the fluid measuring hose and the fluid sampling position, wherein the measuring fluid connection comprises the adapter tube and the perpendicularly or obliquely positioned connection tube in addition to the fluid measuring hose.

11. A connection device in accordance with claim 1, wherein the patient-side connection piece and the adapter are permanently or rigidly connected to one another.

12. A connection device in accordance with claim 1, wherein the adapter tube is permanently or rigidly connected to the patient-side end section of the fluid measuring hose.

13. A connection device in accordance with claim 1, wherein the fluid measuring hose passes through the interior of the supply hose.

14. A connection device in accordance with claim 13, wherein the supply hose is configured as a multi-lumen supply hose, wherein the multi-lumen supply hose provides at least two lumina, which are fluid-tightly separated from one another, and wherein the fluid measuring hose passes through one of the lumina.

15. A connection device in accordance with claim 1, wherein the adapter tube holder is located radially inward of the patient-side connection piece with respect to a longitudinal axis of the patient-side connection piece.

16. A system comprising:

a patient-side coupling unit; and a connection device connected to the patient-side coupling unit, the connection device comprising:

a supply hose connected to or connectable to a medical device;

a patient-side connection piece connected to the supply hose, wherein the supply hose and the patient-side connection piece together are configured to establish at least one a fluid connection between the medical device and the patient-side coupling unit;

a flexible fluid measuring hose;

an adapter comprising a rigid adapter tube and an adapter tube holder, wherein the rigid adapter tube is in fluid communication with the patient-side connection piece, wherein the patient-side connection piece holds the adapter tube holder, wherein the adapter tube holds a patient-side end section of the fluid measuring hose, wherein the adapter tube holder at least partially encloses the adapter tube and holds the end section of the fluid measuring hose, which end section is held by the adapter tube in a predefined position relative to the patient-side connection piece, wherein the connection device is configured to establish a measuring fluid connection comprising the fluid measuring hose between a fluid measuring device and a predefined fluid sampling position, which fluid sampling position is located in an interior of the patient-side connection piece, and wherein a patient-side end of the adapter tube is located at the fluid sampling position.

17. A system according to claim 16, further comprising:

a medical device; and a fluid measuring device, wherein the fluid measuring device is in a data connection with the medical device at least from time to time, wherein the supply hose establishes a fluid connection between the medical device and a patient, and wherein the connection device establishes a measuring fluid connection comprising the fluid measuring hose between the fluid measuring device and a predefined fluid sampling position.

18. A process for manufacturing a connection device the process comprising the steps of:

providing a connection device comprising: a supply hose connected to or connectable to a medical device; a patient-side connection piece connected to the supply hose, wherein the supply hose and the patient-side connection piece together are configured to establish a fluid connection between the medical device and the patient-side coupling unit; a flexible fluid measuring hose; an adapter comprising a rigid adapter tube and an adapter tube holder, wherein the rigid adapter tube is in fluid communication with the patient-side connection piece, wherein the patient-side connection piece holds the adapter tube holder, wherein the connection device is configured to establish a measuring fluid connection comprising the fluid measuring hose between a fluid measuring device and a predefined fluid sampling position, which is located in an interior of the patient-side connection piece, and wherein a patient-side end of the adapter tube is located at the fluid sampling position;

pushing the fluid measuring hose into the supply hose such that a patient-side end section of the fluid measuring hose protrudes over the supply hose after the pushing in;

moving the adapter relative to the supply hose such that the protruding patient-side end section of the fluid measuring hose is pushed into the adapter tube during the movement;

connecting the adapter to the patient-side connection piece; and connecting the adapter to the supply hose, wherein the adapter tube holder at least partially encloses the adapter tube and holds the end section of the fluid measuring hose, which end section is held by the adapter tube in a predefined position relative to the patient-side connection piece.

19. A process in accordance with claim 18, wherein the fluid measuring hose passes through the interior of the supply hose.

20. A process in accordance with claim 19, wherein the supply hose is configured as a multi-lumen supply hose;

wherein the multi-lumen supply hose provides at least two lumina, which are fluid-tightly separated from one another; and the fluid measuring hose passes through one of the lumina.

* * * * *